(12) United States Patent
Reimer (10) Patent No.: US 10,571,431 B2
(45) Date of Patent: Feb. 25, 2020

(54) COMBINATION SENSOR (71) Applicant: SSI Technologies, Inc., Janesville, WI (US)

(72) Inventor: Lawrence B. Reimer, Georgetown, SC (US)

(73) Assignee: SSI TECHNOLOGIES, LLC, Janesville, WI (US)

( * ) Notice: Subject to any disclaimer, the term of this patent is extended or adjusted under 35 U.S.C. 154(b) by 81 days.

(21) Appl. No.: 15/612,640

(22) Filed: Jun. 2, 2017

(65) Prior Publication Data
US 2018/0348167 A1 Dec. 6, 2018

(51) Int. Cl.
G01N 29/22 (2006.01)
G01N 29/024 (2006.01)
G01N 29/32 (2006.01)

(52) U.S. Cl.
CPC ......... *G01N 29/024* (2013.01); *G01N 29/222* (2013.01); *G01N 29/326* (2013.01); *G01N 2291/011* (2013.01); *G01N 2291/0226* (2013.01); *G01N 2291/0228* (2013.01); *G01N 2291/02836* (2013.01); *G01N 2291/02863* (2013.01); *G01N 2291/045* (2013.01)

(58) Field of Classification Search
CPC .... G01N 29/024; G01N 29/222; G01N 29/34; G01N 2291/011; G01N 2291/0226; G01N 2291/0228; G01N 2291/02836; G01N 2291/02863; G01N 2291/02881; G01F 23/263; G01F 23/266; G01F 23/296; G01F 23/2962; G01F 23/2968
USPC .... 73/597, 335.04, 862.337, 862.626, 25.03, 73/25.05, 866.5, 335.05
See application file for complete search history.

(56) References Cited

U.S. PATENT DOCUMENTS

| 4,166,257 | A | 8/1979 | Subramanian |
|---|---|---|---|
| 5,877,997 | A | 3/1999 | Fell |
| 9,052,227 | B1 * | 6/2015 | Lassota ................. G01F 23/268 |
| 2009/0271129 | A1 | 10/2009 | Monmont et al. |
| 2010/0224452 | A1 * | 9/2010 | Jokinen ................. H02H 3/025 187/276 |
| 2011/0301883 | A1 | 12/2011 | Murphy |
| 2012/0000285 | A1 * | 1/2012 | Waga .................... G01N 27/225 73/335.04 |
| 2013/0298699 | A1 * | 11/2013 | Potasek ................. G01L 9/0048 73/862.626 |
| 2013/0331703 | A1 | 12/2013 | Miyake |
| 2014/0041442 | A1 | 2/2014 | Heinrich et al. |
| 2014/0060177 | A1 | 3/2014 | Kline |
| 2017/0350769 | A1 * | 12/2017 | Nonogaki ................ G01K 7/32 |

FOREIGN PATENT DOCUMENTS

WO WO-2016104659 A1 * 6/2016 ............... G01K 7/32

OTHER PUBLICATIONS

United States Patent Office Action for U.S. Appl. No. 16/283,262 dated Sep. 9, 2019 (16 pages).

* cited by examiner

Primary Examiner — Suman K Nath
(74) Attorney, Agent, or Firm — Michael Best & Friedrich LLP (57) ABSTRACT A fluid sensor including a sensing area configured to receive a fluid. The fluid sensor includes a transducer and a capacitive sensor. The transducer is configured to output an ultrasonic wave through the fluid. The capacitive sensor includes a capacitive plate configured to reflect the ultrasonic wave toward the transducer.

17 Claims, 9 Drawing Sheets

COMBINATION SENSOR

TECHNICAL FIELD

Embodiments relate to sensing characteristics of a fluid.

SUMMARY

Various devices and systems, for example, an internal combustion engine, a braking system, and others, require fluids (for example, oil, fuel, diesel exhaust fluid, brake fluid, transmission fluid, washer fluid, refrigerant, etc.). Often, a system requirement is that these fluids meet certain quantities or characteristics, for example, level, temperature, speed-of-sound, concentration, density, and dielectric constant. Often times, sensing various fluid characteristics requires a plurality of sensing elements or sensors (for example, a sensor to sense temperature and a different sensor to sense concentration).

Thus, one embodiment provides a combination sensor with which multiple characteristics of a fluid may be measured. One example provides a fluid sensor including a sensing area configured to receive a fluid. The fluid sensor includes a transducer and a capacitive sensor. The transducer is configured to output an ultrasonic wave through the fluid. The capacitive sensor includes a capacitive plate configured to reflect the ultrasonic wave toward the transducer.

Another embodiment provides a fluid sensor including a housing, a sensing area, a capacitive plate, a substrate, and a controller. The housing includes a continuous surface having a first side and a second side. The sensing area is configured to receive a fluid. The capacitive plate has a first surface and a second surface. The first surface is configured to contact the fluid and the second surface is proximate the first side of the continuous surface. The substrate is proximate the second side of the continuous surface. The controller is electrically coupled to the substrate. The controller is configured to apply an input power to the substrate, determine a relative deviation of an output power, and output a signal based on the relative deviation Yet another embodiment provides a method of determining a dielectric constant of a fluid. The method includes providing a housing including a continuous surface having a first side and a second side. The method further includes providing a capacitive plate having a first surface and a second surface. The first surface is configured to contact the fluid and the second surface is proximate the first side of the continuous surface. The method further includes providing a substrate proximate the second side of the continuous surface. The method further includes applying an input power to the substrate, determining, via a controller, a relative deviation of an output power, and outputting, via the controller, a signal based on the relative deviation.

Other aspects of various embodiments will become apparent by consideration of the detailed description and accompanying drawings.

DETAILED DESCRIPTION

Before any embodiments are explained in detail, it is to be understood that these embodiments are not limited in their application to the details of construction and the arrangement of components set forth in the following description or illustrated in the following drawings. Other embodiments are possible and the embodimens described are capable being practiced or of being carried out in various ways.

The phrase "series-type configuration" as used herein refers to a circuit arrangement in which the described elements are arranged, in general, in a sequential fashion such that the output of one element is coupled to the input of another, though the same current may not pass through each element. For example, in a "series-type configuration," additional circuit elements may be connected in parallel with one or more of the elements in the "series-type configuration." Furthermore, additional circuit elements can be connected at nodes in the series-type configuration such that branches in the circuit are present. Therefore, elements in a series-type configuration do not necessarily form a true "series circuit."

Additionally, the phrase "parallel-type configuration" as used herein refers to a circuit arrangement in which the described elements are arranged, in general, in a manner such that one element is connected to another element, such that the circuit forms a parallel branch of the circuit arrangement. In such a configuration, the individual elements of the circuit may not have the same potential difference across them individually. For example, in a parallel-type configuration of the circuit, two circuit elements in parallel with one another may be connected in series with one or more additional elements of the circuit. Therefore, a circuit in a "parallel-type configuration" can include elements that do not necessarily individually form a true "parallel circuit."

Figure 1:
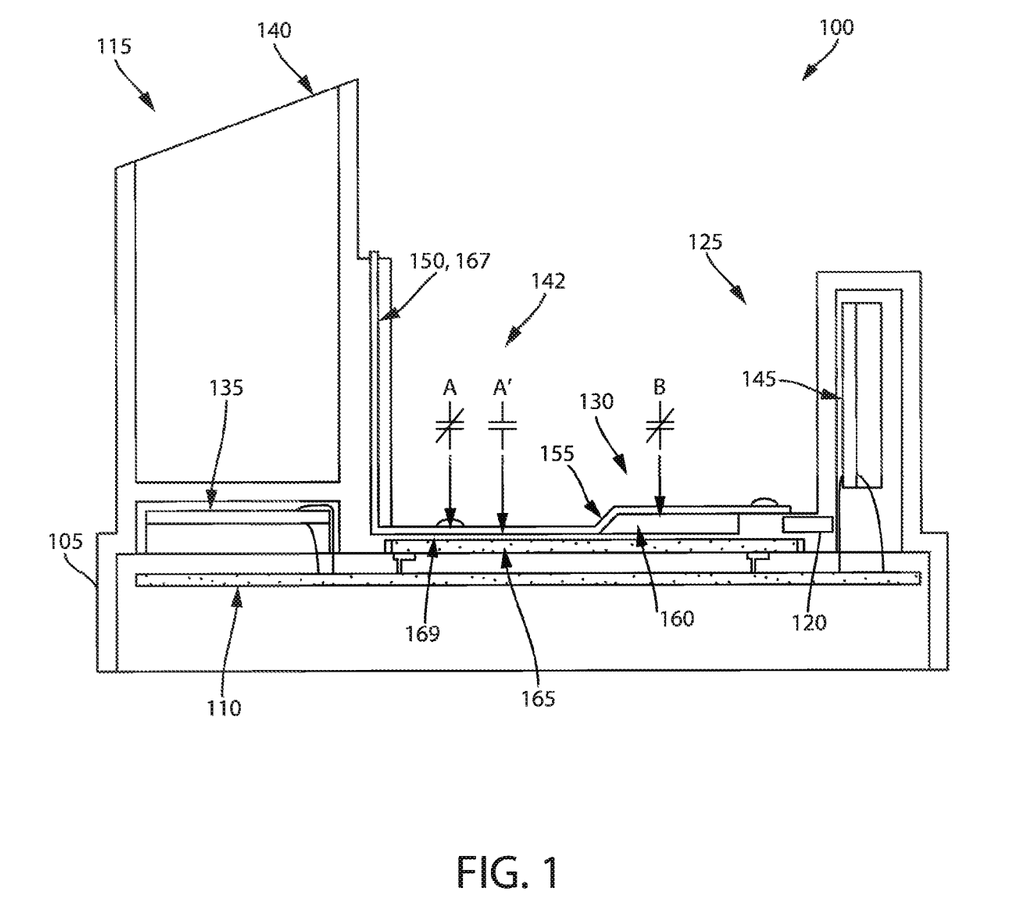
FIG. 1 illustrates a side view of a sensing system according to some embodiments.
Figure 2:
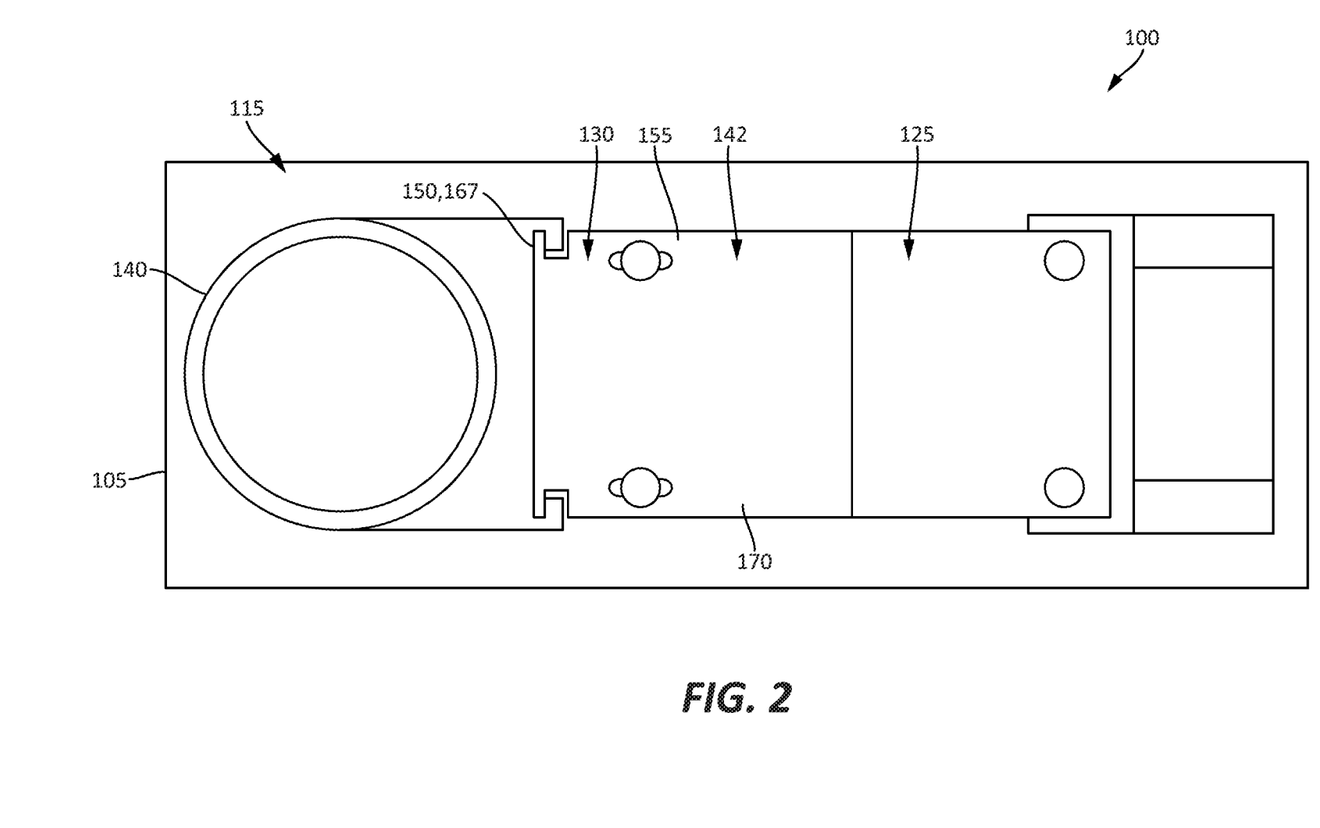
FIG. 2 illustrates a top view of the sensing system of FIG. 1 according to some embodiments.

FIGS. 1 and 2 illustrate a sensing system 100. In some embodiments, the sensing system 100 is placed within a tank holding a fluid to be sensed. In certain instances, the sensing system 100 is placed on a bottom of the tank. The sensing system 100 senses one or more characteristics of the fluid within the tank. The fluid may be, for example, oil, fuel, diesel exhaust fluid, brake fluid, transmission fluid, washer fluid, refrigerant, water (for example, distilled water), etc. The sensing system 100 includes a housing 105, a main substrate, or printed-circuit board, 110, a level sensor 115, a temperature sensor 120, a speed-of-sound sensor 125, and a capacitive sensor 130. The housing 105 may be formed or otherwise constructed from a plastic or similar material. As will be described below, the printed-circuit board includes or has mounted thereon control electronics.

The printed-circuit board (PCB) 110 is electrically and/or communicatively connected to the level sensor 115, the temperature sensor 120, the speed-of-sound sensor 125, and the capacitive sensor 130. In some embodiments, the PCB 110 includes, or is electrically coupled to, a sensor control system 300 (FIG. 6), which, among other things, provides power to the plurality of sensors, analyzes data from the plurality of sensors, and outputs the analyzed data to other components such as an external device (for example, a control system of a vehicle).

The level sensor 115 senses a level of the fluid within the tank. Information regarding the level of the fluid along with information regarding the volume of the container in which the fluid is stored may be used to determine a quantity of the fluid. In the illustrated embodiment, the level sensor 115 includes a level transducer 135 and a level focus tube 140. The level transducer 135 acts as both a transmitter and receiver. In some embodiments, the level transducer 135 is an ultrasonic transducer, such as but not limited to, piezo-electric ultrasonic transducer (PZT). Some embodiments may also include a float. In such an embodiment, the float floats on the surface of the fluid contained within the tank and is configured to reflect acoustic wave signals. The level transducer 135 generates an acoustic wave signal, which propagates through the fluid contained within the level focus tube 140. The acoustic wave signal propagates toward the surface of the fluid. The acoustic wave signal reflects off of the surface of the fluid, contained within the level focus tube 140, and travels back toward the level transducer 135.

Figure 6:
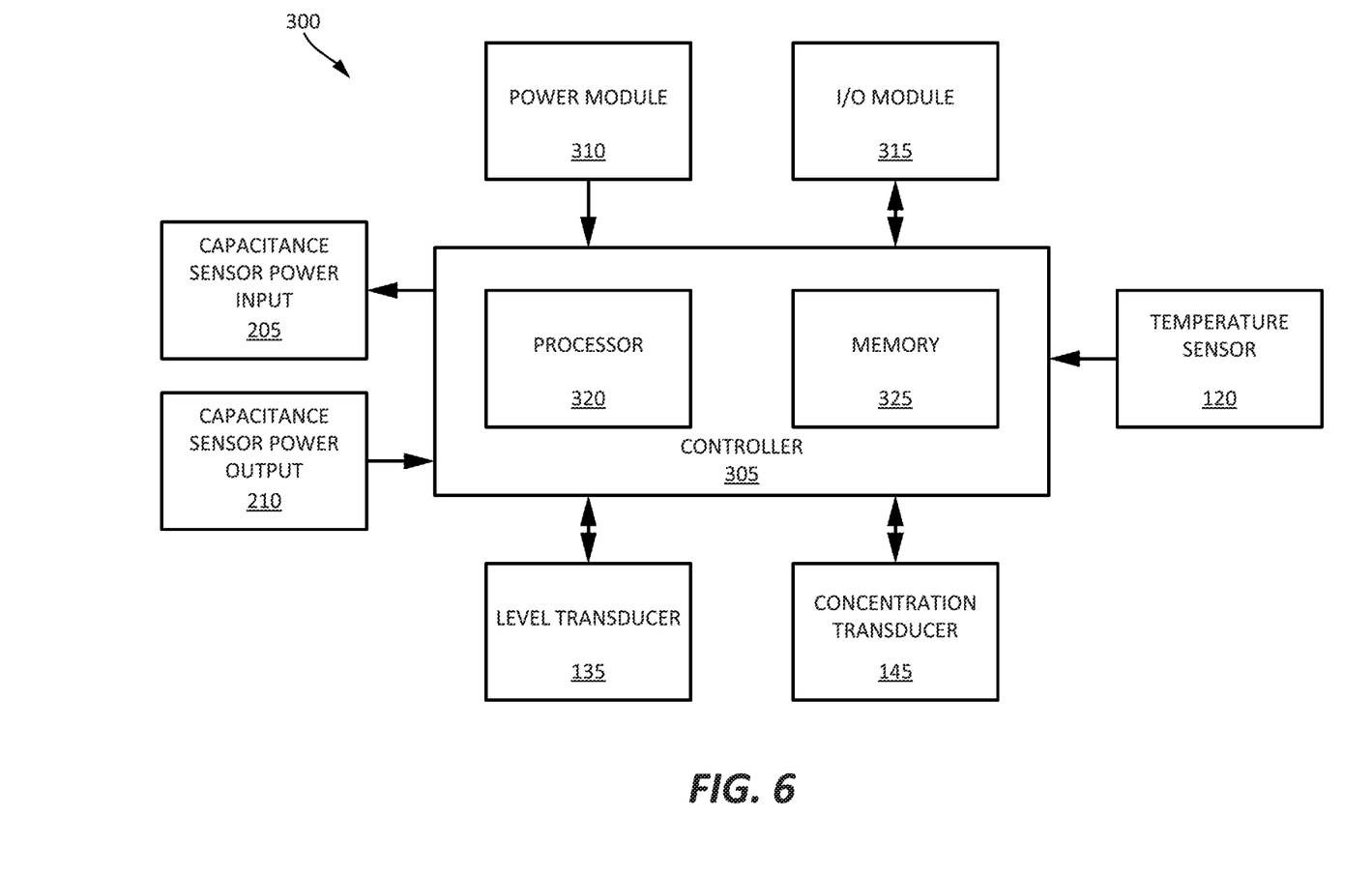
FIG. 6 is a block diagram illustrating a control system of the sensing system of FIG. 1 according to some embodiments.

The temperature sensor 120 senses a temperature of the fluid within the tank. In one embodiment the temperature sensor 120 is a thermocouple. In another embodiment, the temperature sensor 120 is a thermistor. In yet another embodiment, the temperature sensor 120 is a resistance temperature sensor. In yet another embodiment, the temperature sensor 120 is an infrared temperature sensor. The temperature sensor 120 outputs the sensed temperature to the control system 300 (FIG. 6). In some embodiments, the level sensor 115 and the temperature sensor 120 are combined into a combination sensor capable of sensing both a level and a temperature.

The speed-of-sound sensor 125 is configured to sense a speed-of-sound, of the fluid within the tank. A sensed speed-of-sound may be used to determine a quality of the fluid, for example, a specific gravity of the fluid. The speed-of-sound sensor 125 includes a sensing area 142, a speed-of-sound transducer 145, and a reflector 150. The speed-of-sound transducer 145 acts as both a transmitter and receiver. In some embodiments, the speed-of-sound transducer 145 is an ultrasonic transducer, for example, a piezo-electric ultrasonic transducer (PZT). In operation, the speed-of-sound transducer 145 generates an acoustic wave signal, which propagates through the fluid toward the reflector 150. The acoustic wave signal reflects off of the reflector 150 and travels back toward the speed-of-sound transducer 145.

The capacitive sensor 130 determines a dielectric constant of the fluid within the tank. The capacitive sensor 130 includes a capacitive plate 155, a sensing channel 160, and a capacitive substrate 165. As illustrated in FIG. 1, a portion 167 of the capacitive plate 155 acts as the reflector 150, and is configured to reflect the acoustic wave signal back toward the speed-of-sound transducer 145. The capacitive plate 155 of the capacitive sensor 130 is in contact with, or proximate, the housing 105. In some embodiments, the capacitive plate 155 is in contact with a continuous surface, or portion, 169 (FIG. 3) of the housing 105. For example, the continuous portion of the housing 105 is an unbroken portion of the housing 105 having no through-holes. In some embodiments, the capacitive substrate 165 is a printed-circuit board (PCB).

Figure 3:
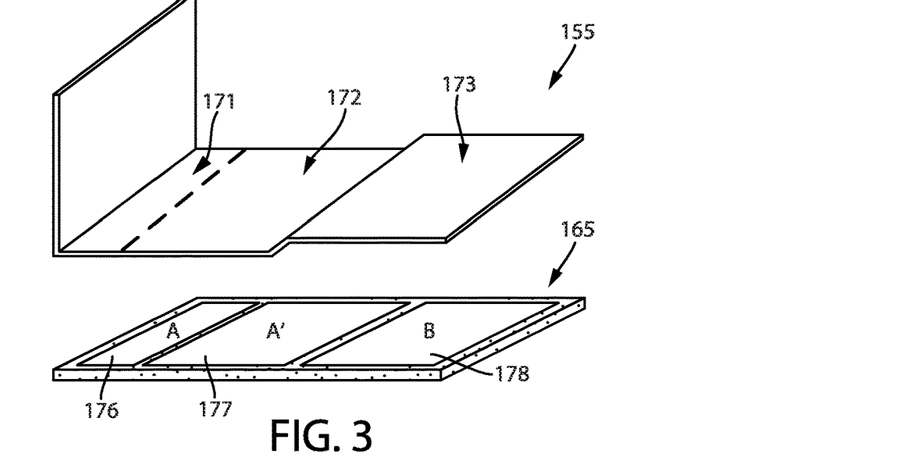
FIG. 3 is an exploded view illustrating a capacitive plate and a capacitive substrate of the sensing system of FIG. 1 according to some embodiments.

FIG. 3 illustrates an exploded view of the capacitive plate 155 and the capacitive substrate 165. As illustrated, the capacitive plate 155 includes a first portion 171, a second portion 172, and a third portion 173. Additionally, as illustrated, the capacitive substrate 165 includes a first plate 176, a second plate 177, and a third plate 178. In some embodiments, the first plate 176, the second plate 177, and the third plate 178 are formed of copper or a similar material. In some embodiments, the first plate 176, the second plate 177, and the third plate 178 are etched into the capacitive substrate 165. In some embodiments, the surface area of the second plate 177 approximately four times to approximately five times larger than the surface area of the first plate 176.

Figure 4:
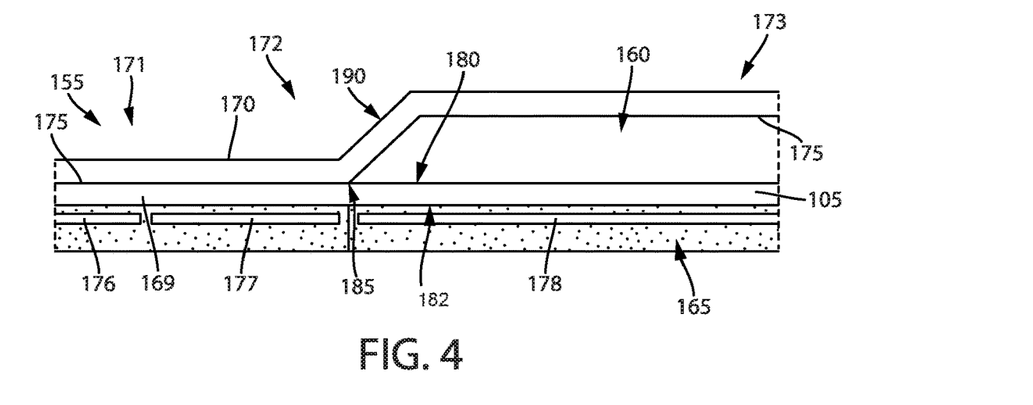
FIG. 4 is an enlarged view illustrating the capacitive plate and housing of the sensing system of FIG. 1 according to some embodiments.

FIG. 4 illustrates an enlarged view of the capacitive plate 155, sensing channel 160, and capacitive substrate 165. In some embodiments, the capacitive plate 155 is formed of copper or a similar material. The capacitive plate 155 includes a first surface 170 and a second surface 175. The first surface 170 is exposed to the sensing area 142 and is configured to contact the fluid contained within the sensing area 142. The second surface 175, of the first and second portions 171, 172, is in contact with, or proximate to, the continuous portion 169 of the housing 105, while the second surface 175, of the third portion 173, is exposed to fluid within the sensing channel 160. As illustrated, the capacitive plate 155 is proximate a first side 180 of the housing 105, while the substrate 165 is proximate a second side 182, opposite the first side 180, of the housing 105.

The capacitive plate 155, the sensing channel 160, and the capacitive substrate 165 form a plurality of capacitors. For example, a first capacitor A (FIG. 4) is formed by the first portion 171, of the capacitive plate 155, and the first plate 176, with the housing 105 (for example, continuous portion 169 of the housing 105) acting as an insulator. The second capacitor A' (FIG. 4) may be formed by the second portion 172, of the capacitive plate 155, and the second plate 177, with the housing 105 (for example, continuous portion 169 of the housing 105) acting as an insulator. The third capacitor B may be formed by the third portion 173, of the capacitive plate 155, and the third plate 178, with the housing 105 (for example, continuous portion 169 of the housing 105) and fluid within the sensing channel 160 acting as insulators. During operation, the fluid to be sensed may flow into the sensing channel 160, thus the third capacitor may be formed by the third portion 173, of the capacitive plate 155, and the third plate 178, with the housing 105 (for example, continuous portion 169 of the housing 105) and the fluid contained within sensing channel 160 acting as insulators.

In some embodiments, a seal 185 is configured to prevent fluid from entering between the first and second portions 171, 172, of the capacitive plate 155, and the housing 105. In the illustrated embodiment, the seal 185 is located between the second portion 172 and the first portion 171. In some embodiments, the seal 185 may be formed of a rubber or polymer material. In other embodiments, the seal 185 may be formed of an epoxy.

In the illustrated embodiment, the capacitive plate 155 further includes a slope, or angled, portion 190. In the example illustrated, the angled portion 190 is configured to reflect any stray speed-of-sound acoustic wave signals, such that the stray speed-of-sound acoustic wave signals do not interfere with detection of the reflected speed-of-sound acoustic wave signals discussed above.

Figure 5:
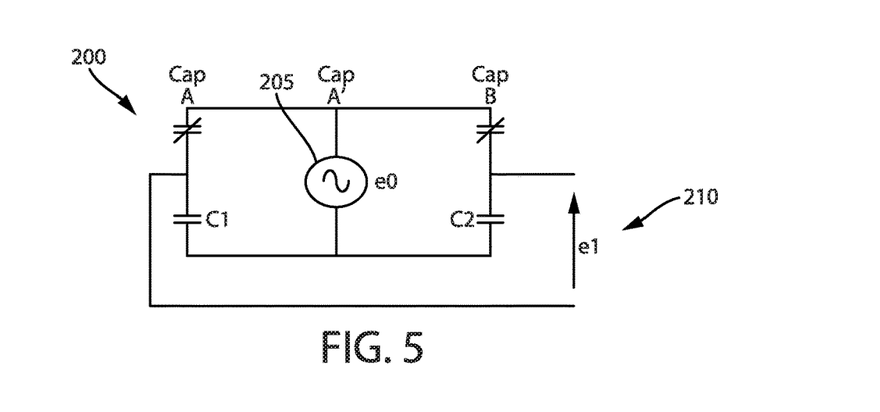
FIG. 5 is a circuit diagram modeling circuitry of the sensing system of FIG. 1 according to some embodiments.

FIG. 5 is a circuit diagram modeling a circuit 200 of the sensing system 100 according to some embodiments of the application. As illustrated, circuit 200 models a capacitive sensor power input 205, capacitor A, capacitor A', capacitor B, capacitor C1, capacitor C2, and a capacitive sensor output 210. As illustrated, in some embodiments, capacitor A' may have an alternating current (AC) behavior similar to that of a short circuit. Such behavior may be a result of the surface area of the second plate 177 (of capacitor A') being approximately four times to approximately five times larger than the surface area of the first plate 176 (of capacitor A), and the space between the second portion 172 of the capacitive plate 155 and the second plate 177 (of capacitor A') being substantially less than the space between the third portion 173 and the third plate 178 (of capacitor B). In some embodiments, capacitive sensor power input 205 and capacitors C1 and C2 are included in or mounted on the PCB 110. In such an embodiment, PCB 110 is electrically connected to capacitive PCB 110. In other embodiments, PCB 110 and the capacitive substrate 165 are combined into a single PCB.

In the model illustrated, capacitor A is in a series-type configuration with capacitor C1, while capacitor B is in a series-type configuration with capacitor C2. Capacitor A and C1 are in a parallel-type configuration with capacitors B and C2 and capacitive sensor AC (alternating current) voltage input 205. Capacitors C1 and C2 have predetermined capacitance values. In some embodiments, capacitor C1 has a capacitance value approximately equal to the capacitance value of capacitor B, when water is present in the sensing area 142 at a nominal temperature (for example, approximately 30° C.). In some embodiments, capacitor C2 has a capacitance value approximately equal to the capacitance value of capacitor A at the nominal temperature. Capacitor A has a capacitance value dependent temperature, while capacitor B has a capacitance temperature dependent on temperature and the fluid present within the sensing channel 160.

In operation, a dielectric constant of the fluid within the sensing area 142, and thus the sensing channel 160, may be determined based on the capacitance value of capacitor B. The capacitance value of capacitor B may be determined based on: the AC input voltage at capacitive sensor power input 205; the sensed temperature from temperature sensor 120; the capacitance value of capacitor A, which in some embodiments is determined based on the sensed temperature from temperature sensor 120; the predetermined capacitance values of C1 and C2; and the voltage present at capacitive sensor output 210. In some embodiments, the dielectric constant of the fluid within the sensing area 142 may be determined using a look up table stored in memory (for example, memory 325 (FIG. 6)).

In some embodiments, to calibrate the sensing system 100, an ideal fluid is placed in the sensing channel 160 at a nominal temperature (for example, 30° C.). The AC input voltage at capacitive sensor power input 205 may then be adjusted until the voltage present at capacitive sensor output 210 is approximately zero volts AC.

Once calibrated, a fluid to be sensed may then be placed in the sensing channel 160. The voltage present at capacitive sensor output 210 may then be monitored, and any deviation (for example, a positive or negative change in AC voltage) may indicate that the fluid to be sensed is not ideal. A deviation of the voltage present at capacitive sensor output 210 caused by a deviation in temperature may be ruled out by monitoring the sensed temperature from temperature sensor 120. In some embodiments, a look up table may be used to determine that the deviation of the voltage present at capacitive sensor output 210 corresponds to the sensed deviation in temperature. If the deviation of the voltage present at capacitive sensor output 210 is not due to a temperature change, an indication, based on the deviation of the voltage present at capacitive sensor output 210, may then be output to a user. Such an indication may indicate that the fluid is not ideal.

FIG. 6 is a block diagram illustrating a control system 300 of the sensing system 100. In some embodiments, the control system 300 is contained, partially or completely, on the PCB 110. The control system 300 includes a controller 305, a power module 310, an input/output (I/O) module 315. The controller 305 includes a processor 320 and memory 325. The memory 325 stores instructions executable by the processor 320. In some instances, the controller 305 includes one or more of a microprocessor, digital signal processor (DSP), field programmable gate array (FPGA), application specific integrated circuit (ASIC), or the like.

The power module 310 receives power and outputs a nominal power to the control system 300 and controller 305. In the illustrated embodiment, the power module 310 receives power from an external device (for example, a control system of a vehicle). In other embodiments, the power module 310 may receive power from another power source, such but not limited to, a battery and/or a renewable power source. The I/O module 315 provides wired and/or wireless communication between controller 305 and the external device.

The control system 300, via the controller 305, is communicatively coupled to the temperature sensor 120, the level transducer 135, the speed-of-sound transducer 145, capacitive sensor power input 205, and capacitive sensor output 210.

In operation, the controller 305 receives the sensed temperature information from the temperature sensor 120, controls the level transducer 135 and the speed-of-sound transducer 145 to generate the respective acoustic wave signals, and receives indication of sensed echoes by the level transducer 135 and the speed-of-sound transducer 145. The controller 305 then calculates a level time-of-flight (ToF) and a speed-of-sound ToF. Using the sensed temperature, the level ToF, and the speed-of-sound ToF, the controller 305 may calculate a level, and thus a quantity, of the fluid as well as a speed-of-sound, and thus a quality, of the fluid. In some embodiments, the speed-of-sound sensor 125 may further determine a specific gravity of the fluid using the sensed temperature and the speed-of-sound ToF.

Additionally, in operation, the controller 305, via capacitive sensor power input 205, outputs an alternating-current (AC) power having a predetermined voltage (for example, approximately 3 VAC to approximately 5 VAC) and senses a voltage at capacitive sensor output 210. The controller 305 may calculate a dielectric constant of the fluid based on the sensed voltage at capacitive sensor output 210.

Figure 7:
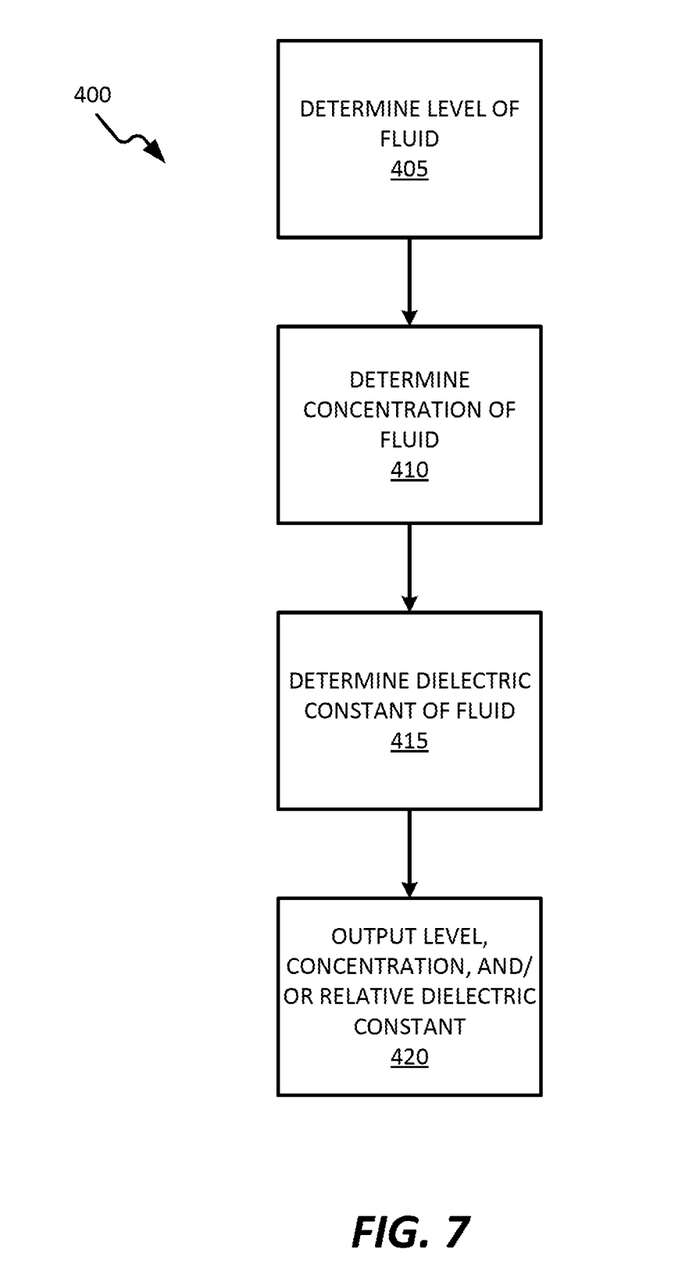
FIG. 7 is a flow chart illustrating a process of the sensing system of FIG. 1 according to some embodiments.

FIG. 7 is a flow chart illustrating an operation, or process, 400 of the sensing system 100 according to some embodiment. It should be understood that the order of the steps disclosed in process 400 could vary. Although illustrated as occurring in parallel order, in other embodiments, the steps disclosed may be performed in serial order. Furthermore, additional steps may be added (for example, diagnostics) to the process and not all of the steps may be required. The sensing system 100 determines a level of the fluid using the level sensor 115 (block 405). The sensing system 100 determines a speed-of-sound of the fluid using the speed-of-sound sensor 125 (block 410). The sensing system 100 determines a relative dielectric constant of the fluid using the capacitive sensor 130 (block 415). The sensing system 100 outputs the level, speed-of-sound, and/or the relative dielectric constant (block 420).

Figure 8:
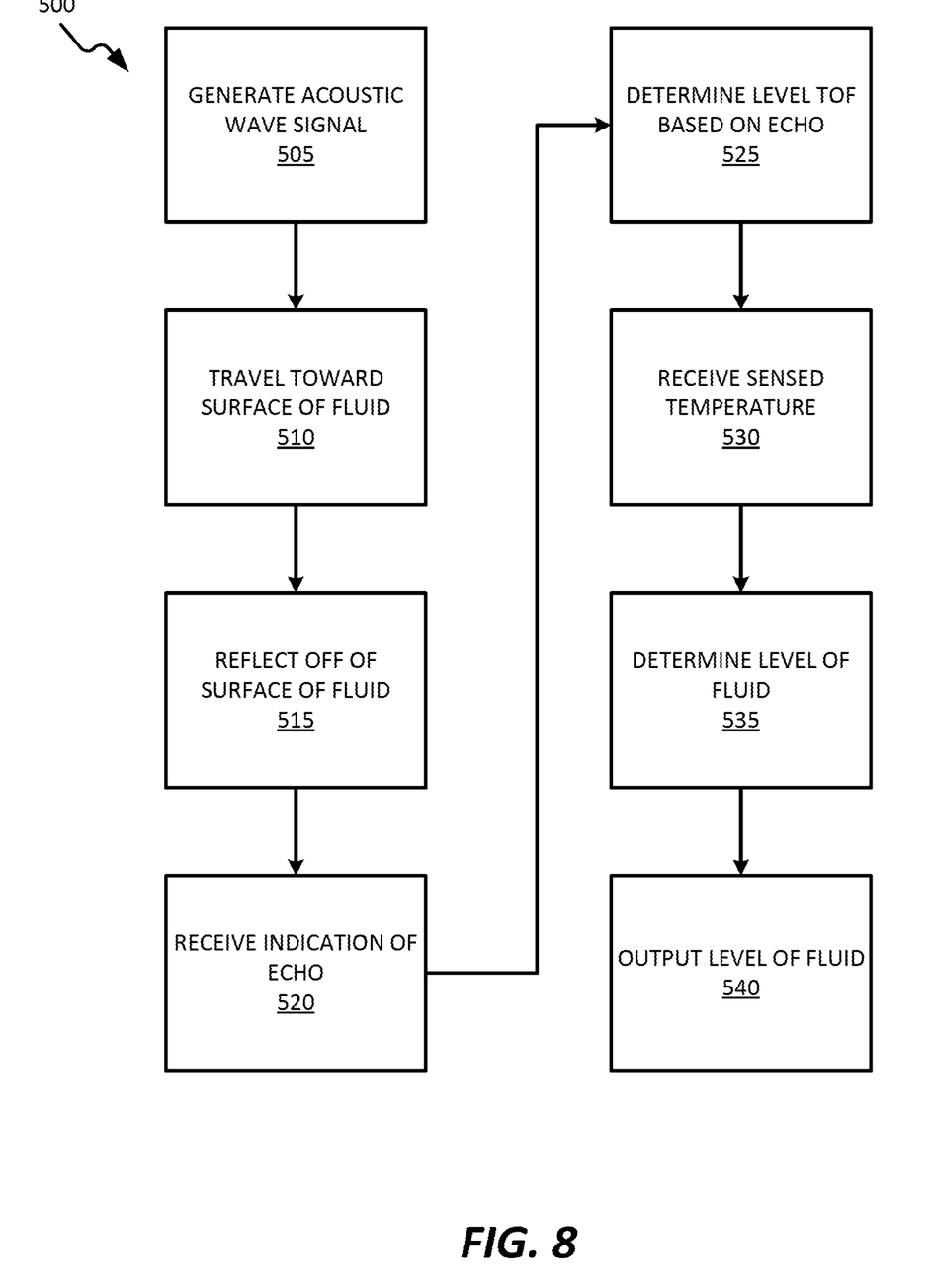
FIG. 8 is a flow chart illustrating a process of the sensing system of FIG. 1 according to some embodiments.

FIG. 8 is a flow chart illustrating an operation 500 for sensing a level of the fluid according to some embodiments. It should be understood that the order of the steps disclosed in process 500 could vary. Furthermore, additional steps may be added to the process and not all of the steps may be required. Controller 305 controls the level transducer 135 to generate an acoustic wave signal (block 505). The acoustic wave signal travels toward a surface of the fluid contained within the focus tube 140 (block 510). The acoustic wave signal reflects off of the surface and travels back toward the level transducer 135 as one or more echoes (block 515). The controller 305 receives an indication that one or more echoes have been received by the level transducer 135 (block 520). The controller 305 determines a level ToF based on the received one or more echoes (block 525). The controller 305 receives a sensed temperature of the fluid from the temperature sensor 120 (block 530). The controller 305 determines a level of the fluid based on the level ToF, the sensed temperature, and a speed-of-sound of the fluid (block 535). In some embodiments, the controller 305 further determines a quantity of the fluid based on the level ToF, the sensed temperature, the speed-of-sound of the fluid, and a known dimension of the tank. In some embodiments, the speed-of-sound of the fluid may be determined by the speed-of-sound sensor 125. The controller 305 then outputs the level and/or quantity of the fluid (block 540).

Figure 9:
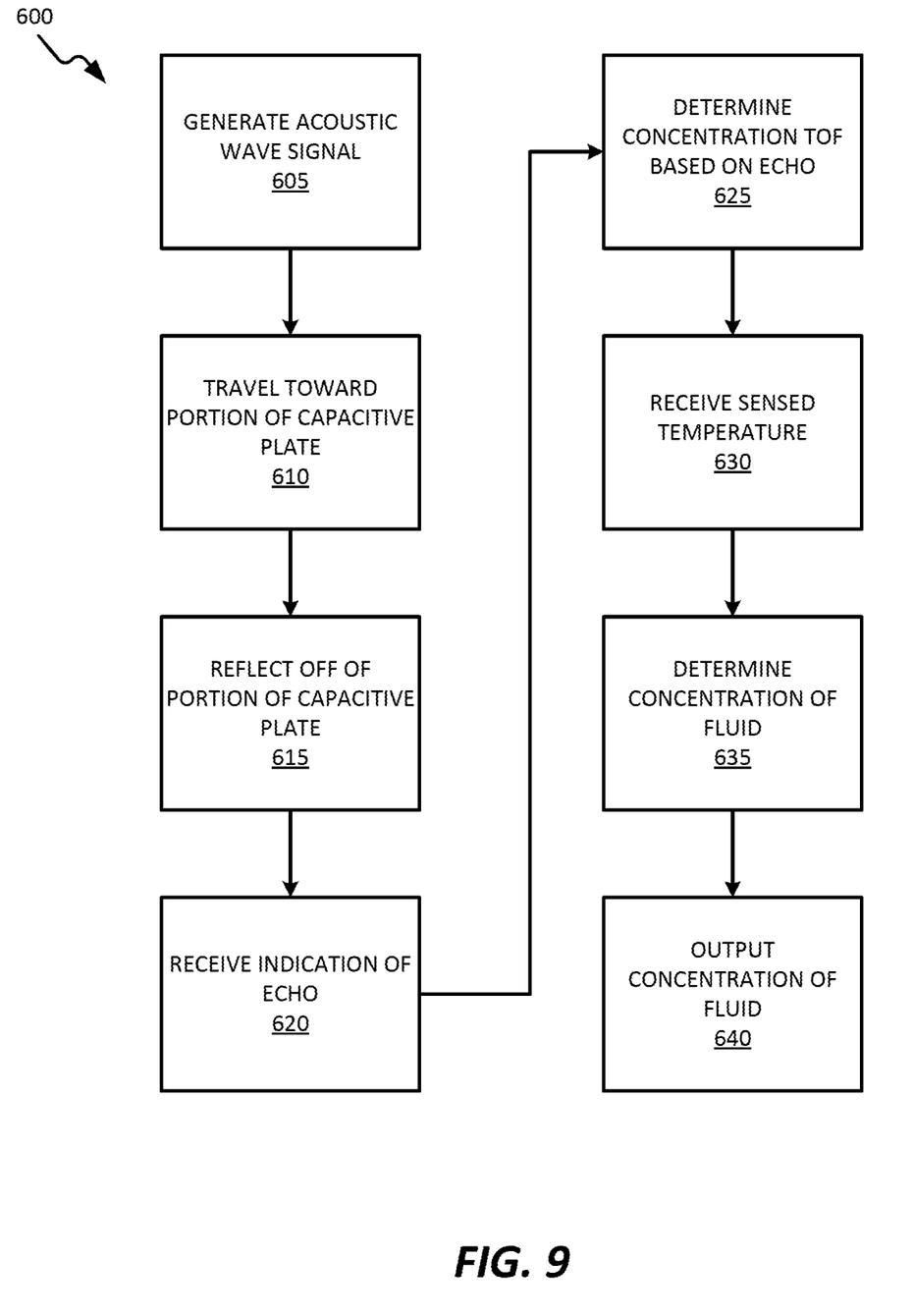
FIG. 9 is a flow chart illustrating a process of the sensing system of FIG. 1 according to some embodiments.

FIG. 9 is a flow chart illustrating an operation 600 for sensing a speed-of-sound of the fluid according to some embodiments. It should be understood that the order of the steps disclosed in process 600 could vary. Furthermore, additional steps may be added to the process and not all of the steps may be required. Controller 305 controls the speed-of-sound transducer 145 to generate an acoustic wave signal (block 605). The acoustic wave signal travels toward portion 167 of the capacitive plate 155 (block 610). The acoustic wave signal reflects off of portion 167 and travels back toward the speed-of-sound transducer 145 as one or more echoes (block 615). The controller 305 receives an indication that one or more echoes have been received by the speed-of-sound transducer 145 (block 620). The controller 305 determines a speed-of-sound ToF based on the received one or more echoes (block 625). The controller 305 receives a sensed temperature of the fluid from the temperature sensor 120 (block 630). The controller 305 determines a speed-of-sound of the fluid based on the level ToF and the sensed temperature (block 635). In some embodiments, the controller 305 further determines a quality of the fluid based on the speed-of-sound ToF and the sensed temperature. The controller 305 then outputs the speed-of-sound and/or quality of the fluid (block 640).

Figure 10:
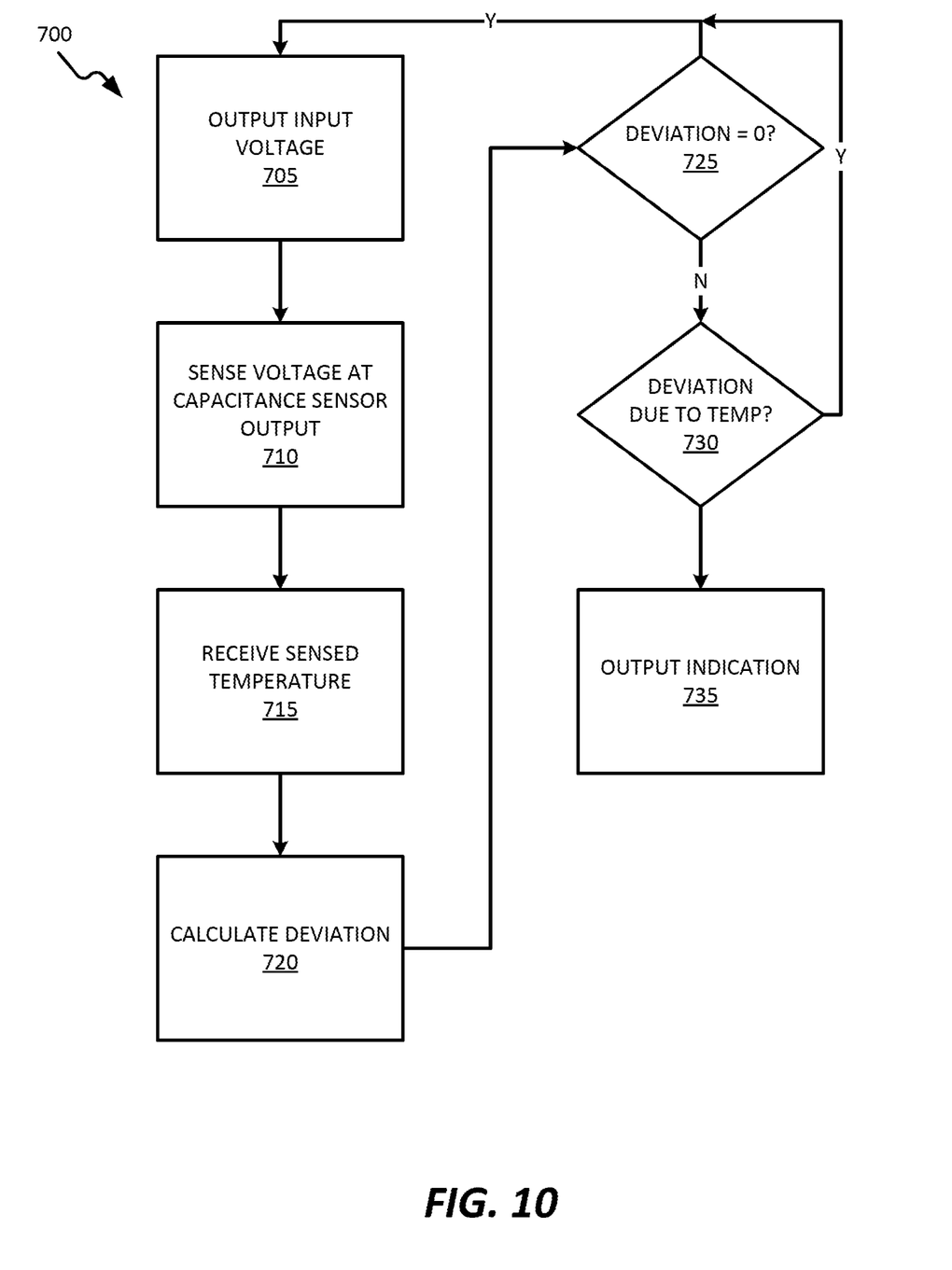
FIG. 10 is a flow chart illustrating a process of the sensing system of FIG. 1 according to some embodiments.

FIG. 10 is a flow chart illustrating an operation 700 for sensing a dielectric constant of the fluid according to some embodiments. It should be understood that the order of the steps disclosed in process 700 could vary. Furthermore, additional steps may be added to the process and not all of the steps may be required. The controller 305 outputs an input voltage (via capacitive sensor power input 205) to capacitor A, capacitor B, capacitor C1, and capacitor C2 (block 705). The controller 305 senses a voltage present at capacitive sensor output 210 (block 710). The controller 305 receives a sensed temperature of the fluid from the temperature sensor 120 (block 715). The controller 305 calculates a relative deviation of the voltage present at capacitive sensor output 210 from zero volts AC (block 720). The controller 305 determines if the relative deviation is equal to approximately zero (block 725). If the relative deviation is approximately zero, operation 700 cycles back to block 705.

If the relative deviation is not equal to approximately zero, the controller 305 determines if the relative deviation is due to a change in temperature (block 730). In some embodiments, the controller 305 determines if the relative deviation is due to a change in temperature by using a look up table. If the relative deviation is due to a change in temperature, operation 700 cycles back to block 705. If the relative deviation is not due to a change in temperature, an indication it output to the user (block 735). In some embodiments, the indication informs the user that the fluid is not ideal.

Figure 11:
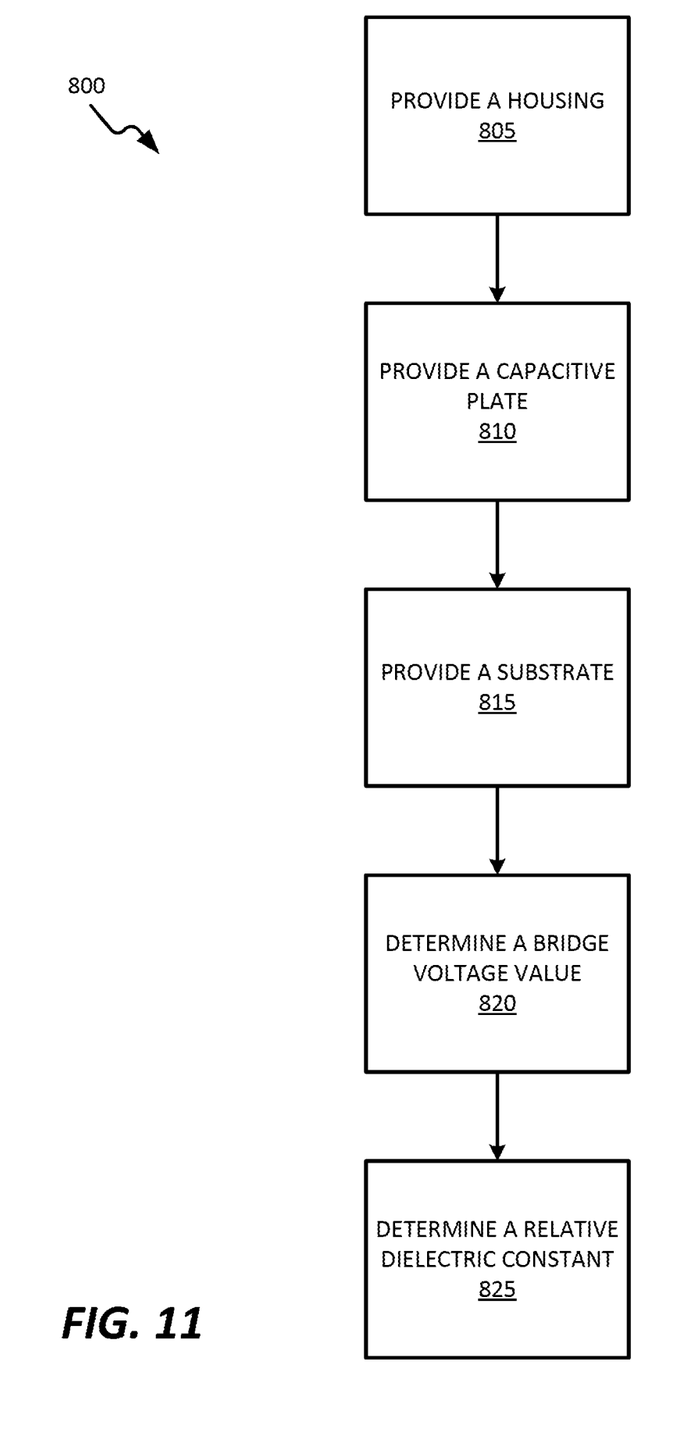
FIG. 11 is a flow chart illustrating a process for providing the sensing system of FIG. 1 according to some embodiments.

FIG. 11 is a flow chart illustrating an operation 800 for providing a system configured to sense a relative dielectric constant of the fluid. It should be understood that the order of the steps disclosed in process 800 could vary. Furthermore, additional steps may be added to the process and not all of the steps may be required. The housing 105 including the continuous surface 169 having a first side and a second side is provided (block 805). The capacitive plate 155 having a first surface and a second surface is provided (block 810). As discussed above, in some embodiments, the first surface is configured to contact a fluid to be sensed, while the second surface is proximate the first side of the continuous surface 169. Substrate 165 is then provided proximate the second side of the continuous surface 169 (block 815). A capacitance value between the capacitive plate 155 and the substrate 165 is determined (block 820). A relative dielectric constant of the fluid is determined based on the capacitance value (block 825).

Thus, embodiments provide, among other things, a sensor configured to determine a level and/or quantity, a speed-of-sound and/or quality, and a dielectric constant of a fluid. Various features and advantages of certain embodiments are set forth in the following claims.

What is claimed is:
1. A fluid sensor comprising:
 a housing including a continuous portion having a first side and a second side;
 a sensing area comprising a sensing channel configured to receive a fluid;
  a first capacitive plate having a first surface and a second surface, wherein the first surface is configured to contact the fluid and the second surface is proximate the first side of the continuous portion of the housing;
 a substrate proximate the second side of the continuous portion of the housing, wherein the substrate includes three capacitive plates; and
 a controller electrically coupled to the substrate, the controller configured to
  apply an input voltage to a sensor power input connected to the three capacitive plates of the substrate,
  measure an output voltage when the fluid is placed in the sensing channel;
  determine a deviation of the output voltage relative to a reference voltage, and
  output a signal based on the deviation of the output voltage.

2. The fluid sensor of claim 1, further comprising the sensing channel between a portion of the second surface of the first capacitive plate and the continuous portion of the housing.

3. The fluid sensor of claim 2, wherein the controller is further configured to determine a capacitance value between the portion of the second surface of the first capacitive plate and a capacitive plate of the substrate.

4. The fluid sensor of claim 3, wherein the substrate is a printed-circuit board.

5. The fluid sensor of claim 1, wherein the controller is further configured to output voltage to the capacitive plates of the substrate and sense an output voltage across the first capacitive plate.

6. The fluid sensor of claim 1, wherein a portion of the first capacitive plate is configured to reflect an acoustic wave signal propagated in the sensing area.

7. The fluid sensor of claim 1, wherein the relative deviation is determined based on the output voltage compared to zero volt.

8. The fluid sensor of claim 1, further comprising a sensor configured to sense a temperature of the fluid.

9. The fluid sensor of claim 8, wherein the output signal is further based on the temperature of the fluid.

10. A method for a fluid sensor, the method comprising:
providing a housing including a continuous portion having a first side and a second side;
providing a first capacitive plate having a first surface and a second surface, wherein the first surface is configured to contact the fluid and the second surface is proximate the first side of the continuous portion of the housing;
providing a substrate proximate the second side of the continuous portion of the housing, wherein the substrate includes three capacitive plates;
receiving a fluid in a sensing area comprising a sensing channel;
applying an input voltage to a sensor power input connected to the three capacitive plates of the substrate;
measuring an output voltage when the fluid is placed in the sensing channel;
determining, via a controller, a deviation of the output voltage relative to a reference voltage; and
outputting, via the controller, a signal based on the deviation of the output voltage.

11. The method of claim 10, further comprising providing the sensing channel between a portion of the second surface of the first capacitive plate and the continuous portion of the housing.

12. The method of claim 10, wherein a portion of the first capacitive plate is configured to reflect an acoustic wave signal propagated in the sensing area.

13. The method of claim 10, wherein the substrate is a printed-circuit board.

14. The method of claim 10, wherein the relative deviation is determined based on the output voltage compared to zero volt.

15. The method of claim 10, further comprising sensing, via a temperature sensor, a temperature of the fluid.

16. The method of claim 15, wherein the output signal is further based on the temperature of the fluid.

17. The method of claim 10, wherein the substrate is a printed-circuit board.

* * * * *